US006809085B1

(12) United States Patent
Elson et al.

(10) Patent No.: US 6,809,085 B1
(45) Date of Patent: Oct. 26, 2004

(54) ADHERENT N,O-CARBOXYMETHYLCHITOSAN DRUG DELIVERY DEVICES FOR MOIST TISSUE AND METHODS OF THEIR USE

(75) Inventors: Clive M. Elson, Halifax (CA); Agis Kydonieus, Kendall Park, NJ (US)

(73) Assignee: Chitogenics, Inc., Chatham, NJ (US)

( * ) Notice: Subject to any disclaimer, the term of this patent is extended or adjusted under 35 U.S.C. 154(b) by 507 days.

(21) Appl. No.: 09/610,281

(22) Filed: Jul. 6, 2000

Related U.S. Application Data

(63) Continuation-in-part of application No. 09/315,480, filed on May 20, 1999.

(51) Int. Cl.$^7$ ............................................. A61K 31/73
(52) U.S. Cl. ................................... 514/55; 536/20
(58) Field of Search ........................... 514/55; 536/20

(56) References Cited

U.S. PATENT DOCUMENTS

| | | | |
|---|---|---|---|
| 4,424,346 A | 1/1984 | Hall et al. ................. | 536/20 |
| 4,603,695 A | * 8/1986 | Ikada et al. ............ | 128/334 R |
| 4,615,697 A | 10/1986 | Robinson ................. | 604/890 |
| 4,619,995 A | 10/1986 | Hayes ..................... | 536/20 |
| 4,659,700 A | 4/1987 | Jackson ................... | 514/55 |
| 4,868,113 A | 9/1989 | Jaye et al. ............... | 435/70 |
| 4,886,787 A | 12/1989 | De Belder et al. ...... | 514/57 |
| RE33,375 E | 10/1990 | Luck et al. .............. | 514/2 |
| 4,978,332 A | 12/1990 | Luck et al. .............. | 604/20 |
| 5,080,893 A | 1/1992 | Goldberg et al. ........ | 514/57 |
| 5,093,319 A | 3/1992 | Higham et al. .......... | 514/55 |
| 5,234,915 A | 8/1993 | Mathur et al. ........... | 514/57 |
| 5,510,102 A | 4/1996 | Cochrum ................. | 424/78 |
| 5,578,661 A | * 11/1996 | Fox et al. ................ | 524/27 |
| 5,679,658 A | 10/1997 | Elson ...................... | 514/55 |
| 5,840,777 A | * 11/1998 | Eagles et al. ............ | 521/62 |
| 5,851,461 A | * 12/1998 | Bakis et al. ............. | 264/50 |
| 5,888,988 A | * 3/1999 | Elson et al. ............. | 514/55 |
| 6,197,325 B1 | * 3/2001 | MacPhee et al. ........ | 424/426 |
| 6,224,794 B1 | * 5/2001 | Amsden et al. ......... | 264/4.1 |

FOREIGN PATENT DOCUMENTS

| | | | |
|---|---|---|---|
| DE | 19604180 A1 | * | 8/1997 |
| DE | 19724869 A1 | * | 12/1998 |
| EP | 0 312 208 | | 4/1989 |
| EP | 0 368 253 | | 5/1990 |
| EP | 0 637 450 | | 2/1995 |
| EP | 0 650 999 | | 5/1995 |
| EP | 0 665 022 | | 8/1995 |
| WO | WO 86/00912 A1 | * | 2/1986 |
| WO | WO 87/07618 A1 | * | 12/1987 |
| WO | WO 93/13137 A1 | * | 7/1993 |
| WO | WO 96/02248 A1 | * | 2/1996 |
| WO | WO 96/02258 A1 | * | 2/1996 |
| WO | WO 96/13282 | | 5/1996 |
| WO | WO 96/13284 | | 5/1996 |
| WO | WO 96.13284 A1 | * | 5/1996 |

OTHER PUBLICATIONS

Tarsi et al., "Inhibition of *Streptococcus mutans* Adsorption to Hydroxyapatite by Low–molecular–weight Chitosans," *Journal of Dental Research*, 76(2), 665–672 (Feb., 1997).*
D. Venes et al. (eds.), *Taber's Cyclopedic Medical Dictionary*, 19th Edition, F. A. Davis Co., Philadelphia, PA, 2001, only pp. 46, 47, 750 and 1077 supplied.*
Aldemann–Grill et al. (1990) "Chemotactic Migration of Normal Dermal Fibroblasts Towards Epidermal Growth Factor and Its Modulation by Platelet–Derived Growth Factor and Transforming Growth Factor–Beta" *Eur. J. Cell Biol.* 51:322–326; (Apr., 1990).
Borah et al. (1995) "Wound Epithelialization is Accelerated by N,O–Carboxymethyl Chitosan" *Amereican Burn Assoc. 27th Annual Mtg.*, Alberquerque, NM;, (Apr. 1995).
Buchholz et al. (1984) "Antibiotic–loaded Acrylic Cement: Current Concepts" *Clin. Orthop. & Rel. Res.* 190:96–108; (Nov., 1984).
Buchholz et al. (1981) "Management of Deep Infection of Total Hip Replacement" *J. Bone & Joint Surgery* 63B(3):342–353.
Canalis et al. (1988) "Growth Factors and the Regulation of Bone Remodeling" *J. Clin. Invest.* 81:277–281; (Feb., 1988).
Chandrasekaran et al. (1982) "Dissolution–Controlled Transport from Dispersed Matrixes" *J. Pharmaceut. Sci.* 71(12): 1399–1402; (Dec., 1982).
Chandy et al. (1991) "Biodegradable Chitosan Matrix for the Controlled Release of Steroids" *Biomat., Art. Cells & Immob. Biotech.* 19(4):745–760.
Christian et al. (1989) "Reconstruction of Large Diaphyseal Defects, without Free Fibular Transfer, in Grade–IIIB Tibial Fractures" *J. Bone & Joint Surg.* 71–A(7): 994–1004; (Aug. 1989).
Dash et al. (1992) "An Implantable Dosage Form for the Treatment of Bone Infections" *Pharmaceutical Research* 9(8):993–1002; (Aug., 1992).
Davies et al. (1988) "N, O–Carboxymethl Chitosan, A New Water Soluble Chitin Derivative" Presented at the 4th Int'l Chitin–Chitosan Conference, Aug. 22–24, Trondheim, Norway.
Golub et al. (1994) "Treating Periodontal Diseases by Blocking Tissue–Destructive Enzymes" *JADA* 125:163–171; (Feb., 1994).
Goodson et al. (1983) "Monolithic Tetracycline–containing Fibers for Controlled Delivery to Periodontal Pockets" *J. Periodontol.* 54(10):575–579; (Oct., 1983).

(List continued on next page.)

Primary Examiner—L. E. Crane
(74) *Attorney, Agent, or Firm*—Palmer & Dodge LLP; Ralph A. Loren, Esq.

(57) ABSTRACT

The present invention relates to drug delivery devices for moist tissue, in particular mucosal tissue and tissue in the serous cavities, as well as a method of its use. The devices, which contain NOCC, are adherent to the mucosal tissue, allowing localized drug delivery. The devices are particularly useful in vaginal, buccal and ocular devices.

14 Claims, 8 Drawing Sheets

OTHER PUBLICATIONS

Greco et al. (1991) "Fibrin–antibiotic mixtures: An in vitro study assessing the possibility of using a biological carrier for local drug delivery" *J. Biomed. Mat. Res.* 25(1):39–51; (Jan., 1991).

Greenhalgh et al. (1990) "PDGF and FGF Stimulate Wound Healing in Genetically Diabetic Mouse" *Amer. J. Pathol.* 136(6): 1235–1246; (Jun., 1990).

Hattori (1990) "Bone Morphogenetic Protein–BMP: Experimental Investigations of Osteogenesis and Chondrogenesis by Implant of BMP–Fibrin Glue Mixture"*J. Jpn. Orthop. Assoc.* 64:824–834 (Sep. 1990).

Hauschka et al. (1986) "Growth Factors in Bone Matrix" *J. Biol. Chem.* 261(27): 12665–12674; (Sep. 25, 1986).

Hayek et al. (1987) "An In Vivo Model For Study of the Angiogenic Effects of Basic Fibroblast Growth Factor" *Biochem. & Biophys. Res. Comm.* 147(2): 876–880; (Sep. 15, 1987).

Higuchi (1963) "Mechanism of Sustained–Action Medication–Theoretical Analysis of Rate of Release of Solid Drugs Dispersed in Solid Matrices" *J. Pharmaceut. Sci.* 52(12): 1145–1149; (Dec. 1963).

Kawamura et al. (1988) "Human Fibrin is a Physiologic Delivery System for Bone Morphogenetic Protein" *Clin. Orthop. & Rel. Res.* 235:302–310; (Oct., 1988).

Klokkevold et al. (1992) "Effect of Chitosan on Lingual Hemostasis in Rabbits with Platelet Dysfunction Induced by Epoprostenol" *J. Oral Maxillofac. Surg.* 50:41–45; (Jan., 1992).

Knighton et al. (1986) "Classification and Treatment of Chronic Nonhealing Wounds" *Ann. Surg.* 204(3): 322–330; (Sep., 1986).

Kram et al. (1991) "Antibacterial Effects of Fibrin Glue–Antibiotic Mixtures" *J. Surg. Res.* 50:175–178; (Feb., 1991).

Kristl et al. (1993) "Hydrocolloids and Gels of Chitosan as Drug Carriers" *Int'l J. Pharmaceut.* 99: 13–19.

Ksander et al. (1990) "The Effect of Platelet Releasate on Wound Healing in Animal Models" *Amer. Acad. Dermatol.* 22(5): 781–791; (May, 1990).

Luyten et al. (1989) "Purification and Partial Amino Acid Sequence of Osteogenin, a Protein Initiating Bone Differentiation" *J. Biol. Chem.* 264(23): 13377–13380; (Aug. 15, 1989).

Lynch et al. (1989) "Growth Factors in Wound Healing" *J. Clin. Invest.* 84:640–646; (Aug., 1989).

Mackey et al. (1982) "Antibiotic Loaded Plaster of Paris Pellets" *Clin. Orthop. & Rel. Res.* 167:263–268; (Jul., 1982).

Majid et al. (1985) "Gentamicin–PMMA Beads in the Treatment of Chronic Osteomyelitis" *Acta. Orthop. Scand.* 56:265–268; (Jun., 1985).

McDermott et al. (1986) "Experimental Use of a New Gentamycin Impregnated Gel" *Canadian Medical Assoc. Conference*, Jun. 1–5, Edmonton (Abstract).

Menaché (1991) "Coagulation Factor IX (human)" in *Hemophilia and Von Willebrand's Disease in the 1990's: A New Decade of Hopes and Challenges*, Lusher et al., eds. (Elsevier Science Publishers B.V., Amsterdam) pp. 301–305; (orig. publ date: Aug. 14–19, 1990).

Menon et al. (1995) "Development of a Composite of Hydroxylapatite and Chitosan as a Bone Graft Substitute" *Proceedings of the 14th southern biomedical Engineering Conference*, Shreveport, LA; (Apr. 7–9, 1995).

Miclau et al. (1993) "In Vitro Pharmakinetics of Antibiotic Release from Locally Implantable Materials" *J. Orthop. Res.* 11:627–632.

Redl et al. (1983) "In Vitro Properties of Mixtures of Fibrin Seal and Antibiotics" *Biomaterials* 4:29–32; (Jan., 1983).

Sakurai et al. (1992) "Controlled Release of Sisomicin from Fibrin Glue" *J. Controlled Release* 18:39–43; (Jan., 1992).

Schlag et al. (1988) "Fibrin Sealant in Orthopedic Surgery" *Clin. Orthop. & Rel. Res.* 227:269–285; (Feb., 1988).

Schrenk et al. (1987) "Fibrin Glue Coating of e–PTFE Prostheses Enhances Seeding of Human Endothelial Cells" *Thorac. Cardiovasc. Surgeon* 35:6–10; (Feb., 1987).

Schultz et al. (1987) "Epithelial Wound Healing Enhanced by Transforming Growth Factor–α and Vaccinia Growth Factor" *Science* 235:350–352; (Jan. 16, 1987).

Schwartz et al. (1989) "The Influence of Fibrin Sealant on Demineralized Bone Matrix–Dependent Osteoinduction" *Clin. Orthop. & Rel. Res.* 238:282–287; (Jan., 1889).

Thacharodi et al. "Release of Nifediphine through Crosslinked Chitosan Membranes" *Int'l J. Pharmaceut.* 96:33–39; (Jul., 1983).

Thompson et al. (1989) "Heparin–binding Growth Factor 1 Induces the Formation of Organoid Neovascular Structures In Vivo" *Proc. Natl. Acad. Sci.* 86:7928–7932; (Oct., 1989).

Thompson et al. (1988) "Site–Directed Neovessel Formation in Vivo" *Science* 241: 1349–1352; (Sep. 9, 1988).

Tsuboi et al. (1990) "Recombinant Basic Fibroblast Growth Factor Stimulates Wound Healing in Healing–impaired db/db Mice" *J. Exp. Med.* 172:245–251; (Jul. 1, 1990).

Urist et al. (1973) "Bone Morphogenesis in Implants of Insoluble Bone Gelatin" *Proc. Natl. Acad. Sci.* 70(12)3511–3515; (Dec., 1973).

Van Brunt et al. (1988) "Growth Factors Speed Wound Healing" *Bio/Tech.* 6:25–29; (Jan., 1988).

Wang et al. (1991) "Bone Morphogenetic Proteins and Bone Repair" *J. Cell. Biochem.* Supp 15F:161; (Apr. 1–7, 1991).

Zilla et al. (1989) "Use of Fibrin Glue as a Substrate for in Vitro Endothelialization of PTFE Vascular Grafts" *Surgery* 105(4):515–522: (Apr., 1989).

Brecht, M. et al., "Increased hyaluronate synthesis is required for fibroblast detachment and mitosis," *Biochem, J.* 239:445–450 (1986).

Docherty, R. et al., "Glycosaminoglycans facilitate the movement of fibroblasts through three–dimensional collagen matrices," *J. Cell Sci.* 92:213–270 (1989).

Hoekstra, D., yaluronan–modified surfaces for medical devices, *Medical devices & diagnostic Industry*, 48–58. (Feb., 1999).

Lynn, L.H. et al., "Effects of hyaluronan on collagen fibrillar matrix contraction by fibroblasts," *J. of Biomedical Materials Research*, 28:123–132 (1994).

* cited by examiner

ADHERENT N,O-CARBOXYMETHYLCHITOSAN DRUG DELIVERY DEVICES FOR MOIST TISSUE AND METHODS OF THEIR USE

REFERENCE TO RELATED APPLICATIONS

This application is a continuation-in-part of U.S. patent application Ser. No. 09/315,480, entitled "ADHESIVE N,O-CARBOXYMETHYLCHITOSAN COATINGS WHICH INHIBIT ATTACHMENT OF SUBSTRATE-DEPENDENT CELLS AND PROTEINS," filed May 20, 1999, the disclosure of which is incorporated herein by reference.

BACKGROUND OF THE INVENTION

A variety of drug delivery devices are known in the art. These include implants, various polymers, microcapsules, liposomes, stents and many hybrids devices. While these drug delivery devices work well in certain body locations, such as skin or muscle tissue, they often fail to work in moist tissue locations. In moist tissue, such as mucosal membranes or tissue in the serous cavities, there is a problem keeping the drug delivery device in place for a sufficiently long time to provide the requisite delivery of the drug at the proper site. While physical methods of keeping the drug delivery device at the proper site, such as the use of sutures have been tried, there may still be problems with controlling the delivery rate or biocompatibility. Accordingly, it has been theorized that an adherent drug delivery device might provide certain benefits.

Various bioadhesives are known in the art. U.S. Pat. No. 4,615,697, issued to Robinson et al., defines a bioadhesive as a material that requires a force of at least about 50 dynes/cm$^2$ to separate two adhered, freshly excised pieces of rabbit stomach, following the procedure disclosed therein. The bioadhesive disclosed in Robinson et al. is a water-swellable, but water insoluble, fibrous, cross-linked carboxy-functional polymer.

The bioadhesives described in the Robinson patent actually show cohesive failure rather than adhesive failure (see Example 1 above). In contrast, the use of NOCC as the bioadhesive in the drug delivery device allows one to tailor the device such that failure of breakaway from tissue can be controlled to be either adhesive or cohesive as desired. In addition, biocompatibility is improved where desired. These devices can also be tailored to provide sustained release of drugs in a controlled manner. In addition, Robinson's polymers are not bioresorbable.

Accordingly, it is an object of the invention to provide new adherent devices and methods of drug delivery to moist tissue.

Another object of the invention is to provide adherent drug delivery devices for use with moist tissue that can be tailored in terms of delivery time and compatibility through the use of additional structural materials.

A further object of the invention is to provide an adherent drug delivery device and methods of their use for buccal, eye, vaginal, gastrointestinal, or intra-serous cavity drug delivery.

A still further object of the invention is to provide an adherent coating that helps prevent the formation of surgical adhesions.

An additional object of the invention is to provide an adherent coating that helps seal tissue.

These and other objects and features of the invention will be apparent from the detailed description and the claims.

SUMMARY OF THE INVENTION

The present invention features a method of utilizing an adherent form of N,O-carboxymethylchitosan ("NOCC") to deliver a series of materials to tissue. The invention is based, in part, on the discovery of adherent coatings of NOCC may be applied to various substrates, such as mammalian tissue, so as to allow delivery of materials such as drugs or hormones to the specific site.

The present invention provides a series of compositions that is adherent to a variety of synthetic materials and mammalian tissues. These compositions can be used as a device for vaginal delivery of hormones, as buccal implants, as eye implants or drug delivery devices and the like for localized or systemic delivery of a variety of materials when adhered to the delivery site.

In one embodiment, the invention provides a composition and method of delivering drugs, proteins, and other therapeutic agents from an adhesive device or composition that is adherent to soft (mucosal or non-mucosal) tissue or hard tissue. In preferred embodiments, the adherent delivery device can be used as a buccal, oral, vaginal, inhalant, or the like delivery system. The device can be in a variety of forms including solutions, creams, pellets, particles, beads, gels, and pastes. In some embodiments, the NOCC is supplemented with a structural support material selected from the group consisting of rubber, plastic, resin, natural and synthetic polymers, and mixtures thereof.

The method is useful for providing sustained release of a drug to moist tissue. The method uses the steps of applying to said moist tissue a drug delivery device which is adherent to said moist tissue and includes a level of N,O-carboxymethylchitosan as a component thereof to provide said adherence. The drug delivery device further containing a sufficient quantity of the drug to be delivered to provide sustained release of said drug and permeation into said moist tissue. The preferred moist tissues are mucosal tissue and tissue within serous cavities. Preferred mucosal tissue is tissue of the oral cavity such as buccal tissue, vaginal tissue, ocular tissue, and gastrointestinal tissue. Preferred tissues within a serous cavity are tissues within the pleural, pericardial or peritoneal cavities.

The method is useful for delivering a number of drugs such as chlorhexidine, tetracycline and mixtures thereof for treatment of buccal problems like mouth sores and periodontal disease or drugs such as melatonin and chlorpheniramine through the buccal mucosa for systemic therapy. The method can also be used to deliver drugs to the vaginal tissue like progestins, estrogens, antifungal agents, antibacterial agents, anti-viral agents, proteins and peptides, particularly levonorgestrel. Similarly, the method can be used to deliver drugs to ocular tissue such as beta blockers and glaucoma treating drugs.

The method of the invention may also provide for adherence or sealing of tissue and prevention of post-surgical adhesions. This method utilizes a medical device that includes NOCC and optionally, a tissue sealant such as a fibrin sealant or a cyanoacrylate. In this case, the preferred moist tissue is at the site of a surgical incision. The primary tissues to be sealed are lung tissues, heart tissues and intestinal tissue.

DETAILED DESCRIPTION OF THE INVENTION

Figure 1:
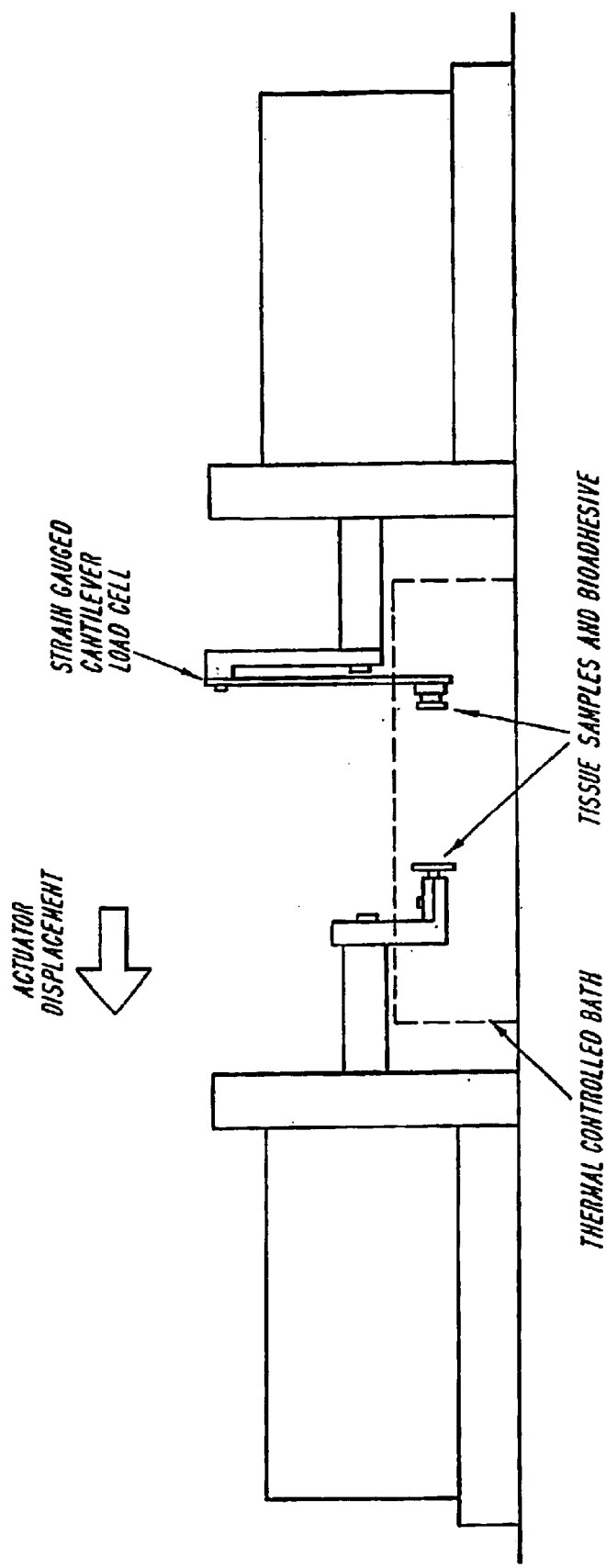
FIG. 1 is a schematic of the apparatus used in Example 1.

The present invention relates to the delivery of a variety of drugs, hormones and the like through the use of a site adherent delivery device. The method of the invention uses an adherent coating of N,O-carboxymethylchitosan ("NOCC") that provides unexpected benefit.

NOCC is a derivative of chitin, which is found in the shells of crustaceans and many insects. Chitin and its derivatives are normally biocompatible, naturally resorbed by the body, and have previously been suggested for use for sustained drug release, bone induction and hemostasis (Chandy and Sharma, Biomat. Art. *Cells & Immob. Biotech.* 19:745–760 (1991); Klokkevold, P. et al., *J Oral Maxillofac. Sur.* 50:41–45 (1992)). Due to its prevalence, chitin may be obtained relatively cheaply, largely from waste products. One of the most useful of the chitin derivatives is NOCC. As disclosed in U.S. Pat. No. 4,619,995, issued to Hayes, NOCC has carboxymethyl substituents on some of both the amino and primary hydroxyl sites of the glucosamine units of the chitosan structure. NOCC may be used in an uncrosslinked form as a solution or may be cross-linked or complexed into a stable gel. Because of its advantageous physical properties, and its relative low cost, NOCC presents advantageous properties for use in site localized delivery systems.

Definitions

The terms "adherent NOCC" or "an adherent coating of NOCC" mean a coating or composition of NOCC that exhibits an adhesion between freshly excised tissues of at least about 100 dynes/cm$^2$, using the procedure described in Example 1.

The term "medical device" means any device which is implanted in the body for medical reasons or which has a portion of the device extending into the body (like a catheter) as well as devices which provide a medical benefit when attached to, or are in contact with, the body. Examples of medical devices include, without limitation, hemostats, tissue sealants, and adhesion prevention barriers.

The term "delivery device" means any type of device that can be used to deliver the contained material at the localized site. The delivery device may be as simple as an adherent paste applied to the site or may be shaped or constructed for the particular application.

The term "drug" means any product which causes an effect in a cell or organism including, but not limited to classic drugs, peptides, proteins, antibodies and the like.

The term "moist tissue" means a tissue that in its normal activity is kept moist. Moist tissue includes mucosal tissue and tissue in the serous cavities.

The adherent NOCC used in the present invention may take many forms. For example, adherent NOCC may be used in a solution, a hydrogel, a paste, a rehydratable film, cream, foam, or a sponge. These forms are prepared by methods well known to those of ordinary skill in the art. The delivery device may have other structural materials as well as NOCC. Some of these include chitosan, carboxymethylcellulose, resins, alginate, rubbers and the like.

The adherent NOCC used in the present invention may be the parent compound or may be cross-linked. Cross-linked adherent NOCC may be either covalently cross-linked or ionically cross-linked. Various methods of cross-linking NOCC are known in the art and are within the scope of this invention. In addition, the degree to which the adherent NOCC is cross-linked may be optimized for specific applications by one of ordinary skill without undue experimentation. It has been found that the degree of cross-linking is roughly inversely proportional to the adhesiveness of the coating. That is, the greater the degree of cross-linking of the adherent NOCC, the lesser degree of adherence; In preferred embodiments, the degree of cross-linking is less than 1:5 (moles cross-linking agent to moles, NOCC monomer), more preferably between 1:100 and 1:1000 on a molar basis.

Figure 2:
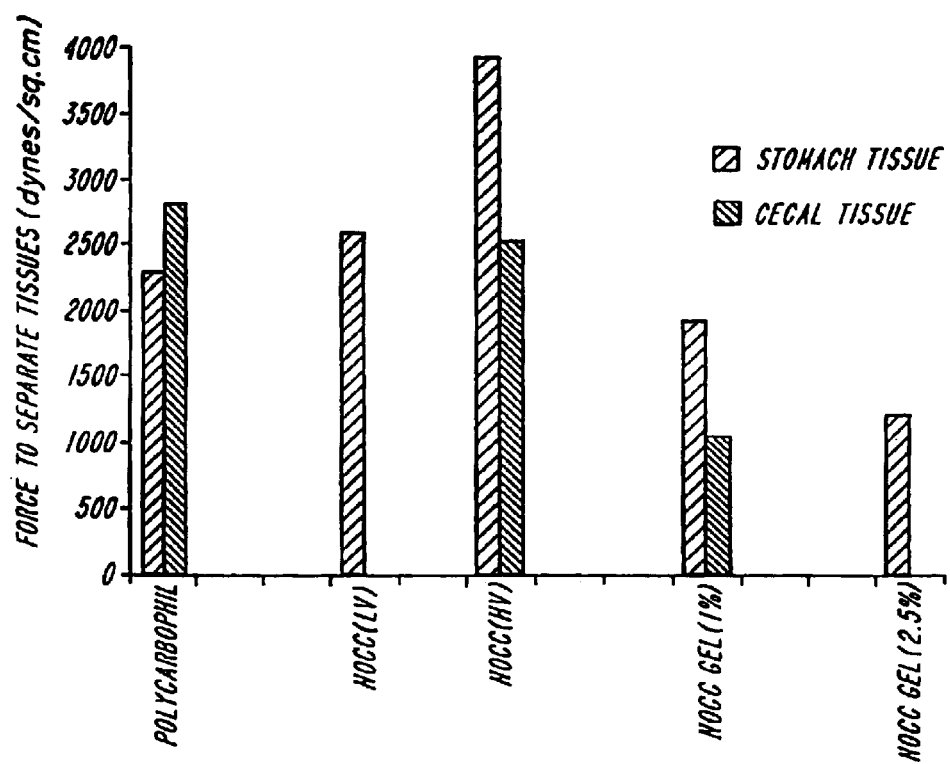
FIG. 2 is a bar graph showing the results of Example 1.

The bioadhesive strength of several adherent NOCCs was compared to that of polycarbophil, a cross-linked acrylic acid polymer available from B.F.Goodrich. As more fully described in Example 1, solutions of low and high viscosity NOCC were prepared, as well as hydrogels of high viscosity NOCC. The bioadhesive was applied to stomach and cecal tissue samples and the bioadhesive strength was measured according to a modified version of the procedure disclosed in U.S. Pat. No. 4,615,697. The transfer of polymer to both tissue surfaces indicated that the adhesive force of the polymer exceeded the cohesive force. A summary of results appears in Tables 1 and 2, and FIG. 2. In preferred embodiments, the bioadhesive strength of adhesive NOCC coatings of the invention is desirably greater than at least about 1000 dynes/cm$^2$, more preferably greater than at least about 2000 dynes/cm$^2$, and most preferably greater than at least about 3000 dynes/cm$^2$.

Both the low viscosity and high viscosity NOCC polymer solutions in citrate buffer behaved similarly to polycarbophil when applied as a coating to the mucosal surface of stomach tissue (Table 1). This was also true for similar solutions of NOCC using phosphate buffered saline instead of citrate buffer as well as non-mucosal, cecal tissue (Table 2). It was observed that as NOCC was cross-linked, the cohesion of the materials increased and the adhesion decreased. The loss of adhesion was dependent on the extent of cross-linking. These findings are likely attributable to the fact that cross-linking adherent NOCC introduced more structure into the polymer, which consequently restricted interactions with the tissue surface. The cross-linking also joined the polymer chains together, resulting in increased cohesiveness.

Figure 5:
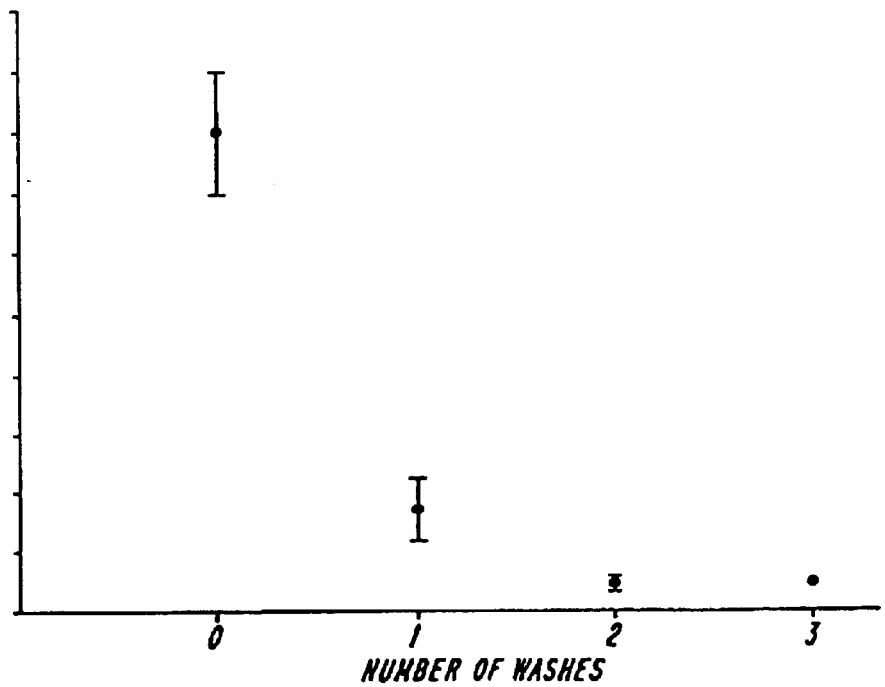
FIG. 5 is graph showing the total volume of $^{125}$I-NOCC adhered to rat femur, as calculated using Equation 3.

The ability of NOCC to adhere to bone tissue was also studied. The results indicate that NOCC adheres to bone tissue (FIG. 5). After the third wash, $9.5 \times 10^{-3 \pm 0.002}$ $\mu$L/mm$^2$ (or about 0.1 $\mu$g NOCC/mm$^2$) of $^{125}$I labeled NOCC remained adhered to the rat femur.

The following, non-limiting examples will further elucidate the invention.

EXAMPLE 1

In this example, the bioadhesive strength of several adherent NOCC coating compositions is compared to that of polycarbophil. Polycarbophil (B.F. Goodrich, Akron, Ohio)

was prepared as a 4% w/v solution in both 0.2 M citrate buffer (pH 4.8) and 0.9% saline (pH 6.8). Low viscosity ("LV") NOCC (240 cps, Brookfield spindle 3, 50–100 rpm) was prepared as 4% w/v solution in citrate buffer (pH 5.6). High viscosity ("HV") NOCC (P78NOCC1) was prepared as 2.5% w/v solution in citrate buffer (pH 5.6). High viscosity NOCC was prepared as 1% and 2.5% in citrate buffer (pH 5.6–5.7), autoclaved and cross-linked (1:500). HV NOCC was also prepared as 2.5% solution in phosphate buffered saline (PBS). Gels were formed from 1% HV NOCC by cross-linking (1:100) in PBS and by cross-linking (1:250) in saline following autoclaving.

Both stomach and cecal tissues from Sprague-Dawley rats were harvested immediately prior to testing and were kept moist in saline solution. Tissue samples were mounted on circular plastic disks with the inner surfaces of stomach tissues and the outer surfaces of cecal tissues exposed. Tissue samples were held in place with a suture around the end of the plastic disks. The plastic disks were obtained from the plungers of 3 and 5 ml syringes; the diameters of the disks were 7.0 (surface area of 38.5 $mm^2$) and 9.5 mm (surface area of 70.9 $mm^2$), respectively. The tissue holders were attached to a cantilever load cell and to the actuator of an MTS servohydraulic material testing machine (see FIG. 1).

The temperature compensated load cell was wired into a Daytronic 3720 Strain Gauge Conditioning Unit in a half bridge configuration. Data collection was performed using a Macintosh Centris 650 computer equipped with lab VIEW software and a 12-bit NB-MIO-16 data acquisition board. The cantilever load cell was calibrated over the working range of 0–3 grams using a series of proving masses (0.1, 0.23, 0.5, 1 to 3.0 g) verified on a Mettler PJ 360 balance. A least squares calibration curve was determined to convert the resulting output from volts to grams force.

The smaller diameter tissue of the pair of fresh tissue samples received 30 $\mu$l of test material. The software was designed to take a zero reading after attaching the tissue samples and applying a coating of the bioadhesive. The testing system actuator was then manually advanced using the displacement potentiometers to bring mating faces into compression while visually monitoring the resulting load level on the computer monitor. The mating faces were allowed to remain compressed at a nominal load of 0.9 g for one minute. The computer then displaced the actuator at a constant rate of 12.0 mm/min, monitoring the distraction force with time. After failure the computer determined the peak distraction load and saved the loading curves to a spreadsheet file.

For repeated testing of the same samples, the tissues were scraped with the side of a syringe needle, rinsed with citrate buffer or water as appropriate and a new aliquot of the same polymer was applied. Fresh tissues were used for each different polymer sample; all samples in citrate buffer were tested on stomach tissue and all samples at neutral pH were tested on cecal tissue. All testing was performed in air.

All polymer samples were applied to the smaller surface area tissue sample at a rate of approximately 1 $\mu$l/$mm^2$. Following distraction of the actuator, the transfer of polymer to both tissue surfaces indicated that the adhesive force of the polymer exceeded the cohesive force. For example, polycarbophil was adhesive to both cecal and stomach tissue and required a tensile force of 2300–2800 dynes/$cm^2$ to cause failure. The failure was cohesive rather than adhesive since polymer was observed on both tissue surfaces after separation. A summary of results appears in Tables 1 and 2 and FIG. 2.

Both the low viscosity and high viscosity adherent NOCC polymer solutions in citrate buffer behaved similarly to polycarbophil when applied as a coating to the mucosal surface of stomach tissue. Both adherent NOCC samples failed cohesively and required larger forces to achieve tissue separation than for polycarbophil. However, when high viscosity NOCC solutions were cross-linked to form hydrogels, they became more cohesive and failed by detaching from the larger diameter disk at forces of 85% (1% gel) and 53% (2.5% gel) of that of polycarbophil.

The strengths of adhesion to the external surface of the cecum (Table 2) again demonstrated that a solution of NOCC (2.5%-high viscosity) was comparable to polycarbophil. It was also observed that as adherent NOCC was cross-linked the cohesion of the materials increased and the adhesion decreased. The loss of adhesion was dependent on the extent of cross-linking.

It should be noted that polycarbophil measured under the present conditions exhibited twice the adhesive force as reported in U.S. Pat. No. 4,615,697. This is presumably due to testing in air rather than in solution. For both stomach and cecal tissues, adherent NOCC solutions were either comparable to or exceeded the performance of polycarbophil: the force required to achieve failure was equal to or larger than that of polycarbophil and failure was due to cohesion not adhesion.

NOCC hydrogels on both types of tissue were adhesive; however, they were significantly less adhesive than materials that were not cross-linked. They demonstrated an adhesive failure rather than cohesive; also it was observed that increasing the extent of cross-linking decreased the adhesive force. These findings were not surprising since cross-linking adherent NOCC introduced more structure into the polymer, which restricted interactions with the tissue surface and also joined the polymer chains together resulting in increased cohesiveness.

Another finding was that both the 2.5% high viscosity NOCC solution and the 1% NOCC gel in citrate were more adhesive than its counterparts in PBS. Without limitation to the present invention, this difference may possibly be explained by the influence of the citric acid environment. At neutral pH, NOCC exists as an anionic species resulting from the presence of negatively charged carboxylate groups (—COO); the free amines on NOCC are primarily uncharged. By contrast, in acidic citrate buffer (pH 5.6) the amine groups are protonated to form positively charged ammonium sites (-$NH_3$+) that ionically bind citrate ions. Such salts are described in U.S. Pat. No. 5,412,081. Since citrate has three carboxylate groups, two of which are negatively-charged at pH 5.6, the net result is that NOCC in acidic citrate has an increased number of carboxylate groups associated with the polymer and, hence, displays an increased bioadhesiveness.

TABLE 1

Bioadhesion of NOCC Formulations to Stomach Tissue.

| Polymer Sample | Tensile Failure Force (grams) | Force to Separate Tissue (dynes/sq.mm) | Adhesive or Cohesive Failure |
|---|---|---|---|
| 4% Polycarbophil | 0.901 ± 0.035 | 2295 ± 170 | Cohesive |
| 4% LV NOCC solution | 1.007 ± 0.107 | 2567 ± 270 | Cohesive |

TABLE 1-continued

Bioadhesion of NOCC Formulations to Stomach Tissue.

| Polymer Sample | Tensile Failure Force (grams) | Force to Separate Tissue (dynes/sq.mm) | Adhesive or Cohesive Failure |
|---|---|---|---|
| 2.5% NOCC (HV) | 1.513 | 3857 | Cohesive |
| 1% NOCC gel | 0.770 ± 0.280 | 1961 ± 410 | Adhesive |
| 2.5% NOCC gel | 0.481 | 1226 | Adhesive |

Notes: Error limits are one average deviation based on 2–3 determination and values without error limits result from a single measurement.

TABLE 2

Bioadhesion of NOCC Formulations to Cecal Tissue.

| Polymer Sample | Tensile Failure Force (grams) | Force to Separate Tissue (dynes/sq.mm) | Adhesive or Cohesive Failure |
|---|---|---|---|
| 4% Polycarbophil | 1.113 | 2837 | Cohesive |
| 2.5% NOCC (HV) solution | 0.992 ± 0.060 | 2567 ± 140 | Cohesive |
| 1% NOCC gel (1:100) | 0.302 ± 0.010 | 770 ± 30 | Adhesive |
| 1% NOCC gel (1:250) | 0.410 | 1045 | Adhesive |

Notes: Error limits are one average deviation based on 2–3 determination and values without error limits result from a single measurement.

EXAMPLE 2

This example illustrates the adherent property of an adherent NOCC coating of the present invention.

Six female rats were anaesthetized using sodium pentobarbital (60 mg/kg) and subsequently sacrificed by cervical dislocation. Twelve femurs were harvested and stripped of connective tissue by sharp dissection. Excess connective tissue was removed from the rat femur by immersing the rat femurs in boiling water for thirty minutes. The femurs were then rinsed and air dried.

Figure 3:
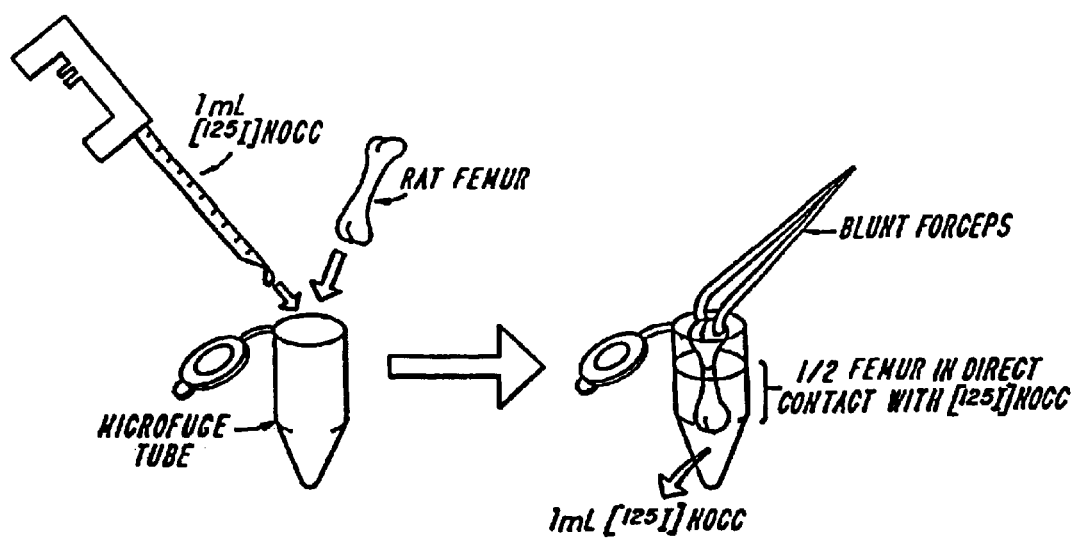
FIG. 3 is a schematic of the procedure used in Example 2.

Each femur was immersed in 1 ml of $^{125}$I labeled NOCC such that half the surface area of the femur was in direct contact with the $^{125}$I NOCC solution (FIG. 3). The other half of the femur was used to manipulate the femur. Subsequently, the femur was either placed directly into a scintillation vial and then placed in a γ- counter rack, or the femur was subjected to a uniform "wash" before being placed into a scintillation vial and the γ- counter rack.

Four groups of three $^{125}$I NOCC treated femurs were subjected to either one wash, two washes, three washes or no washes. A wash consisted of the uniform agitation of the femur in approximately 150 ml of PBS for five seconds. Two washes consisted of a wash, removing the femur from PBS for one second, and then repeating a wash. Hence, three washes consisted of a wash, removal of the femur, a wash, removal of the femur, and one last wash. The PBS solution was replaced for each group of femurs.

Figure 4:
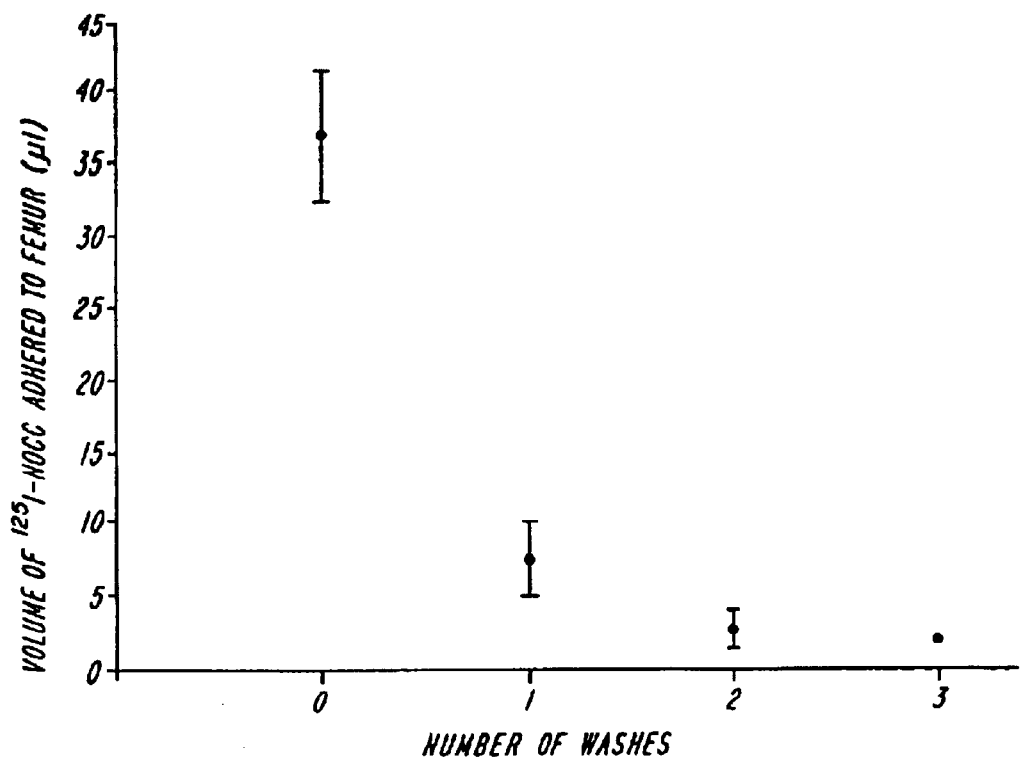
FIG. 4 is graph showing the total volume of $^{125}$I-NOCC adhered to rat femur, as calculated using Equation 1.

The activity of 125I NOCC was evaluated by a Beckman γ-counter. The amount of $^{125}$I NOCC adhered to a rat femur was calculated using Equation 1, which uses the activity of 1 ml of $^{125}$I NOCC (7.2×10$^7$ CPM) and the activity of the $^{125}$I NOCC on the femur, (detected by the γ-counter). The results appear in FIG. 4.

Equation 1:

Volume of $^{125}$I NOCC adhered of femur =

$$\frac{\text{Activity }(CPM)\text{ of sample}}{7.2 \times 10^7 \ CPM} \times 1 \text{ mL}$$

Next, the amount of $^{125}$I NOCC per unit area of the femur was calculated. The surface area that was in direct contact with the $^{125}$I NOCC solution was calculated for one representative rat femur.

Equation 2:

Surface area in direct contact with $^{125}$I NOCC $= \frac{2\pi rh}{2} + \pi r^2$ Where $h$ = the total height of the femur; $r$ = the radius of the femur Where h=the total height of the femur; r=the radius of the femur The amount of $^{125}$I NOCC per unit area of then calculated, using Equation 3, by dividing the surface area of the rat femur in direct contact with $^{125}$I NOCC into the amount of $^{125}$I NOCC adhered to the rat femur. The results appear in FIG. 5.

Equation 3:

$^{125}$I NOCC per unit area of femur =

$$\frac{\mu L \text{ of } ^{125}\text{I NOCC adhered to femur}}{\text{Surface area in direct contact with } ^{125}\text{I NOCC}}$$

The surface area of the rat femur was calculated to be 228 mm$^2$, (radius =2.25 mm and total femur height=30 mm).

Table 3 outlines the number of washes each femur was subjected to, the activity of $^{125}$I NOCC, amount of $^{125}$I NOCC adhered to femur, and the amount of $^{125}$I NOCC per unit area of femur.

TABLE 3

$^{125}$I NOCC adhered to femur

| Femur number | Number of washes/ femur | Activity $^{125}$I NOCC/femur (CPM) | Volume of $^{125}$I NOCC adhered to femur (µL) | Volume of $^{125}$I NOCC (µL)/ unit are of femur (mm$^2$) |
|---|---|---|---|---|
| 1 | 0 | 2.3 × 10$^6$ | 31.9 | 1.4 × 10$^{-1}$ |
| 2 | 0 | 2.7 × 10$^6$ | 37.5 | 1.6 × 10$^{-1}$ |
| 3 | 0 | 2.9 × 10$^6$ | 40.3 | 1.8 × 10$^{-1}$ |
| 4 | 1 | 6.9 × 10$^5$ | 9.6 | 4.2 × 10$^{-2}$ |
| 5 | 1 | 5.1 × 10$^5$ | 7.1 | 3.1 × 10$^{-2}$ |
| 6 | 1 | 3.9 × 10$^5$ | 5.4 | 2.4 × 10$^{-2}$ |
| 7 | 2 | 1.4 × 10$^5$ | 1.9 | 8.3 × 10$^{-3}$ |
| 8 | 2 | 1.4 × 10$^5$ | 1.9 | 8.3 × 10$^{-3}$ |
| 9 | 2 | 2.9 × 10$^5$ | 4.0 | 1.8 × 10$^{-2}$ |
| 10 | 3 | 1.6 × 10$^5$ | 2.2 | 9.6 × 10$^{-3}$ |
| 11 | 3 | 1.3 × 10$^5$ | 1.8 | 7.9 × 10$^{-3}$ |
| 12 | 3 | 1.8 × 10$^5$ | 2.5 | 11.0 × 10$^{-3}$ |

The results indicate that $^{125}$I NOCC adheres to rat femur. After a third wash, it was found that 9.5×10–3+/–0.0002 µL/mm$^2$ (or about 0.1 µg NOCC/mm$^2$) of $^{125}$I NOCC remained adhered to the rat femur.

EXAMPLE 3

In this example, a vaginal cream containing levonorgestrel, a steroid, was prepared. This cream is useful as an intravaginal delivery device.

The NOCC-based cream was prepared with the following composition:

1.56% N,O-Carboxymethylchitosan (NOCC)
 3.1% heavy mineral oil
 9.3% glycerol
 1.5% SPAN 60 (sorbitan monostearate, Atkemix, Inc.)
 0.30% levonorgestrel (Sigma Aldrich)
 84.2% 36 mM citrate buffer (pH 4.2)
 (All percentages are weight to volume.)

The cream was prepared by dissolving solid NOCC in hot citrate buffer and adjusting the pH to 5 with citric acid. Separately, SPAN 60 was warmed and combined with mineral oil, the levonorgestrel was added, and finally the glycerol. The warm NOCC solution was then combined with the levonorgestrel mixture to form the cream.

The resulting cream was homogeneous, easily smeared, and adherent to tissue. The cream contained 3 mg levonorgestrel per gram.

EXAMPLE 4

In this example, a spermicidal and anti-microbial cream containing Nonoxynol-9, a well known spermicide, was prepared. This cream is adherent to mucousal tissue such as vaginal tissue.

A NOCC-based cream was prepared with the following composition:

2.5% N,O-Carboxymethylchitosan (NOCC)
 2.5% hydroxypropylmethyl cellulose (HPMC)
 5% Nonoxynol-9
 0.5% sodium dodecyl sulfate (SDS)
 0.1% Antifoam A (Dow Corning)
 89.4% 36 mM citrate buffer (pH 4.2)
 (All percentages are weight to volume.)

To prepare the cream, the Antifoam A and the Nonoxynol-9 were added to hot citrate buffer. The NOCC and the HPMC were combined in equal weights and then added to the warm citrate buffer mixture and blended. Finally, the solid SDS was combined to form a creamy paste.

The resulting cream was homogeneous, easily smeared, and adherent to tissue.

EXAMPLE 5

In this example, a buccal device containing NOCC and other polymers was prepared. This device is useful as a buccal drug delivery device.

A PVC resin composition was made by diluting a high viscosity (polyvinyl chloride"PVC") resin (available from Plast-o-Meric, Inc) with dioctylphthalate in the ratio of two thirds resin to one third dioctylphthalate.

An alginate paste was prepared having the following composition:

55% sodium alginate
 30% chitosan
 15% PVC resin composition as shown above
 (All percentages are weight to weight.)

A NOCC paste was also prepared having the following composition:

33% NOCC
 33% chitosan
 33% PVC resin composition
 (All percentages are weight to weight.)

The buccal device was prepared by compressing 60 mg of the alginate paste in a hand-held potassium bromide pellet press (Barnes Analytical, Pellet Holder for Handi-Press) to form a pellet. Two mg of the NOCC paste was placed on top of the pellet and the combination was compressed again in the pellet holder. The portion of the pellet coated with the NOCC paste and the sides of the pellet were coated with the PVC resin. The pellet was then cured at 150 C° for several minutes.

The resulting pellet was 7 mm in diameter and 2–3 mm thick and durable with some flexibility. The device contained 1% NOCC, and was adherent to moist tissue.

EXAMPLE 6

The formulation described in Example 5 was modified by incorporating melatonin into the alginate paste component prior to pellet formation. The alginate paste was made 3.3% (w/w) melatonin, with the remaining ingredients having the same proportions. A pellet was then prepared as described in Example 5.

The resulting pellet contained 2 mg of melatonin and was of the same dimensions and physical properties as the device of Example 5. The formulation was adhesive to moist tissue. Using the same approach, pellets containing 4 mg of melatonin were also prepared.

EXAMPLE 7

The formulation described in Example 5 was modified by incorporating chlorpheniramine maleate into the alginate paste component. The alginate paste was made 16.7% (w/w) chlorpheniramine maleate, with the remaining ingredients having the same proportions. A pellet was then prepared as described in Example 5.

The resulting pellet contained 10 mg of chlorpheniramine maleate and was of the same dimensions and physical properties as the device of Example 5. The formulation was adhesive to moist tissue. Using the same approach, pellets containing 5 mg of chlorpheniramine maleate were also prepared.

EXAMPLE 8

In this example, a buccal device similar to that shown in Example 5 was prepared with an increased concentration of NOCC. The general methods and materials are similar to those shown in Example 5.

An alginate paste was prepared having the following composition:

52% sodium alginate
 33% chitosan
 15% PVC resin composition (as prepared in Example 5)
 (All percentages are weight to weight.)

A NOCC paste was also prepared having the following composition:

50% NOCC
 50% PVC resin composition (as prepared in Example 5)
 (All percentages are weight to weight.)

The buccal device was prepared by compressing 70 mg of the alginate paste in a hand-held potassium bromide pellet press (Barnes Analytical, Pellet Holder for Handi-Press). Ten mg of the NOCC paste was placed on top of the pellet and the combination was compressed again in the pellet holder. The portion of the pellet coated with the NOCC paste and the sides of the pellet were coated with the PVC resin composition. The pellet was then cured at 150 C° for several minutes.

The resulting pellet was 7 mm in diameter and 3–3.5 mm thick and durable with some flexibility. The device contained 6% NOCC. The formulation was adhesive to moist tissue.

EXAMPLE 9

In this example, a different buccal device, one having NOCC throughout, was prepared.

A paste was prepared having the following composition:

50% sodium alginate

30% chitosan

4% NOCC

16% PVC resin composition (as prepared in Example 5)

(All percentages are weight to weight.)

The buccal device was prepared by compressing 100 mg of the paste in a hand-held potassium bromide pellet press (Barnes Analytical, Pellet Holder for Handi-Press). The end and sides of the pellet were coated with the PVC resin composition. The pellet was then cured at 150 C° for several minutes.

The resulting pellet was 7 mm in diameter and 3–4 mm thick and durable with some flexibility. The device contained 4% NOCC throughout and was adhesive to moist tissue.

EXAMPLE 10

In this example, a buccal device containing a liquid silicone rubber, rather than a heat-curable plastic, was manufactured.

A paste was prepared with the following composition:

42% sodium alginate

16% chitosan

10% NOCC

32% Silastic® 7-6860 (Dow Corning)

(All percentages are weight to weight.)

The buccal device was prepared by compressing 60 mg of the paste in a hand-held potassium bromide pellet press (Barnes Analytical, Pellet Holder for Handi-Press). A second 60 mg of the paste was placed on top of the pellet and the combination was compressed again in the pellet holder. The entire pellet was then coated with a diluted mixture of liquid silicone rubber (30% Silastic® Q7-4840 plus 70% hexanes). The pellet was then cured at 150 C° for 20 minutes. The pellet was cleaved at the union between the portions of paste to yield two devices with one non-coated surface each.

The device was 7 mm in diameter and 2–3 mm thick; it was durable and somewhat flexible. The device contained 10% NOCC and was adhesive to moist tissue.

EXAMPLE 11

In this example, the buccal devices from the previous examples were tested to determine the time of attachment of the device to the gingiva of test subjects. Table 4 shows the results of these experiments.

TABLE 4

Tests of Various Buccal Devices

| Device | In vivo attachment time |
| --- | --- |
| Example 8. | 32–41 hr |
| Example 9. | 4 hr |
| Example 10. | 13 hr |

These results indicate that adhesive buccal devices incorporating NOCC can be prepared with different thermoplastics and thermoset rubbers. The attachment times can be altered by changing the composition or the method of preparation of the device.

EXAMPLE 12

In this example, the permeation of levonorgestrel (LN) from the NOCC-based vaginal cream of Example 3, was determined.

Previously harvested pieces of rabbit large bowel (surface area 1.767 $cm^2$) were mounted in an Improved Franz Diffusion Cell containing 0.9% saline (13ml) as the receptor medium. The vaginal cream of Example 3 (1.0 g) was applied directly to the rabbit tissue; the experiments were performed in triplicate.

Aliquots of 1.0 ml (which were replaced with fresh saline solution) were withdrawn from the receptor chamber at 1, 3, 6, 20, 24, 48 hours. LN in samples was quantified using high performance liquid chromatography (Hewlett Packard, model 1090,series II, fitted with Hypersil $C_{18}$, 5 µm, 25 cm×4.6 mm column, a UV detector set at 241 nm and an acetonitrile(80%)-water(20%) mobile phase).

Figure 6:
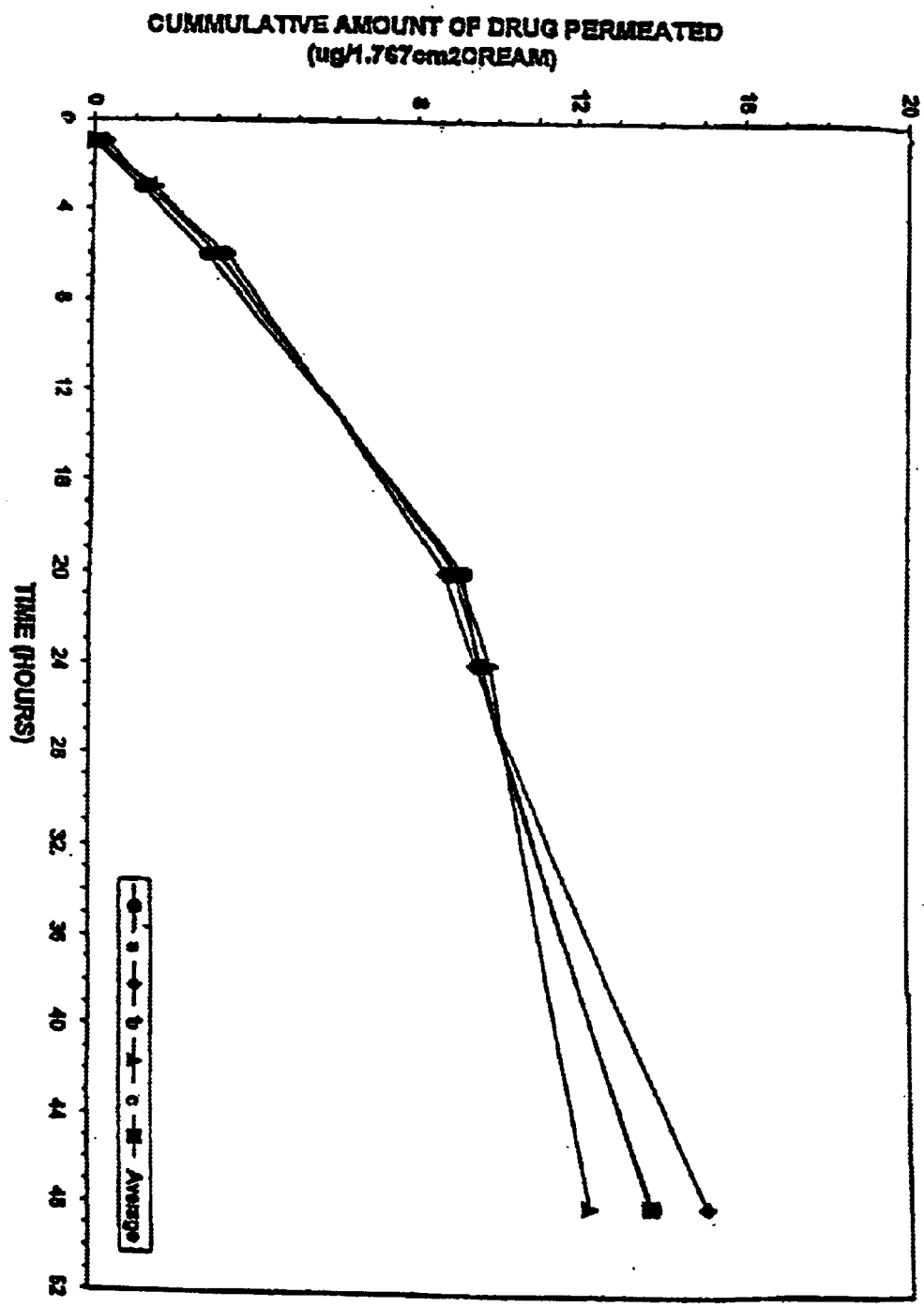
FIG. 6 is a graph showing the in vitro permeation of levonorgestrel from a vaginal cream in a diffusion test chamber.

Accurately weighed portions of the LN-vaginal cream as well as the cream recovered from the diffusion cells were extracted with 20 ml methanol for 16 hr on a wrist-action shaker and analyzed. The in vitro permeation profiles for the 3 mg/g vaginal cream is shown in FIG. 6. The profile demonstrates a near linear release with time over the 48 hr test period. The replicate results along with an average are plotted. The permeation rate of hormone that diffused through the tissue from the cream was very small (0.163±0.010 µg/$cm^2$/hr).

Analysis of the vaginal cream formulation following methanol extraction found 2.964±0.020 mg/g LN in the nominal 3 mg/g cream. The concentration of LN in the creams recovered following the permeation studies were 3.101±0.315 mg/g for the 3 mg/g cream. This confirmed that the bulk of the hormone was retained within the vaginal cream and not released through the tissue membrane.

Vaginal creams based on NOCC released very limited amounts (i.e. less than 0.5%) of levonorgestrel through normal tissue over a 48 hr period. This finding implies that such creams would maintain low levels of systemic hormones in vivo and would allow for the attachment of LN to steroid receptors on the surface of mucosal tissue (local effect). In addition, since these formulations are strongly adherent and insoluble at the acidity of the vagina, NOCC-based vaginal creams appear to be suitable candidates for vaginal delivery devices.

EXAMPLE 13

This example tested the release of melatonin from one of the described buccal devices. The buccal devices containing 2 mg of melatonin described in Example 6 were placed directly onto pieces of previously harvested rabbit large bowel that were mounted in Franz Diffusion Cells as described in Example 12. The permeation studies were conducted as described in Example 12 except that the HPLC analysis was modified; a Spectra Physics, Model SP8800, fitted with Alltima phenyl, 5 micron, 15 cm×4.6 mm column, and a UV detector set at 223 nm was used with an acetonitrile (40%)–0.1% phosphoric acid mobile phase.

Figure 7:
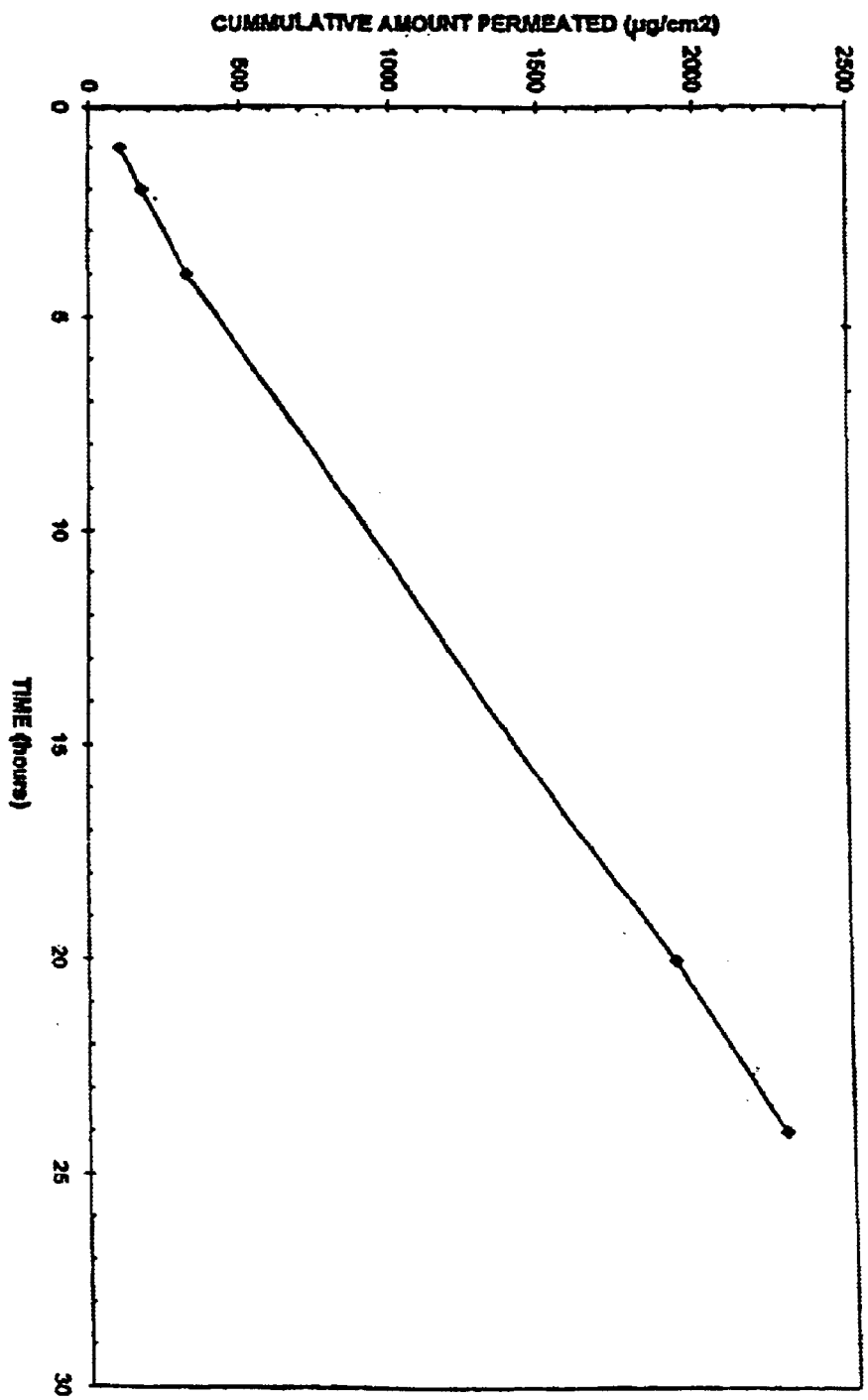
FIG. 7 is a graph showing the in vitro permeation of melatonin from a buccal device in a diffusion test chamber.

The in vitro permeation profile is shown in FIG. 7. The flux can be calculated from this graph by determining its slope. For the device or pellet containing 2 mg of melatonin, the average permeation rate (flux) was 19.5 $\mu g/cm^2/hr$. For the pellet containing 4 mg of melatonin, the flux was approximately the same as for the 2 mg pellet, indicating that even at 2 mg, the pellet is saturated with melatonin. The flux of 19.5 $\mu g/cm^2/hr$ is adequate to produce a systemic therapeutic level of melatonin.

EXAMPLE 14

In this example, the buccal devices of Example 7 were tested for permeation of chlorpheniramine maleate through mucosal membranes in vitro. Several buccal devices, containing chlorpheniramine maleate described in Example 7 were placed directly onto pieces of previously harvested rabbit large bowel that were mounted in Franz Diffusion Cells as described in Example 12. The permeation studies were conducted as described in Example 12 except that the HPLC analysis was modified: a Spectra Physics, Model SP8800, fitted with Alltima C8, 5 micron, 15 cm×4.6 mm column, and a UV detector set at 261 nm with an acetonitrile (30%)–0.05% potassium dihydrogen phosphate plus 1ml of phosphoric acid, pH 2.5 (70%) mobile phase.

Figure 8:
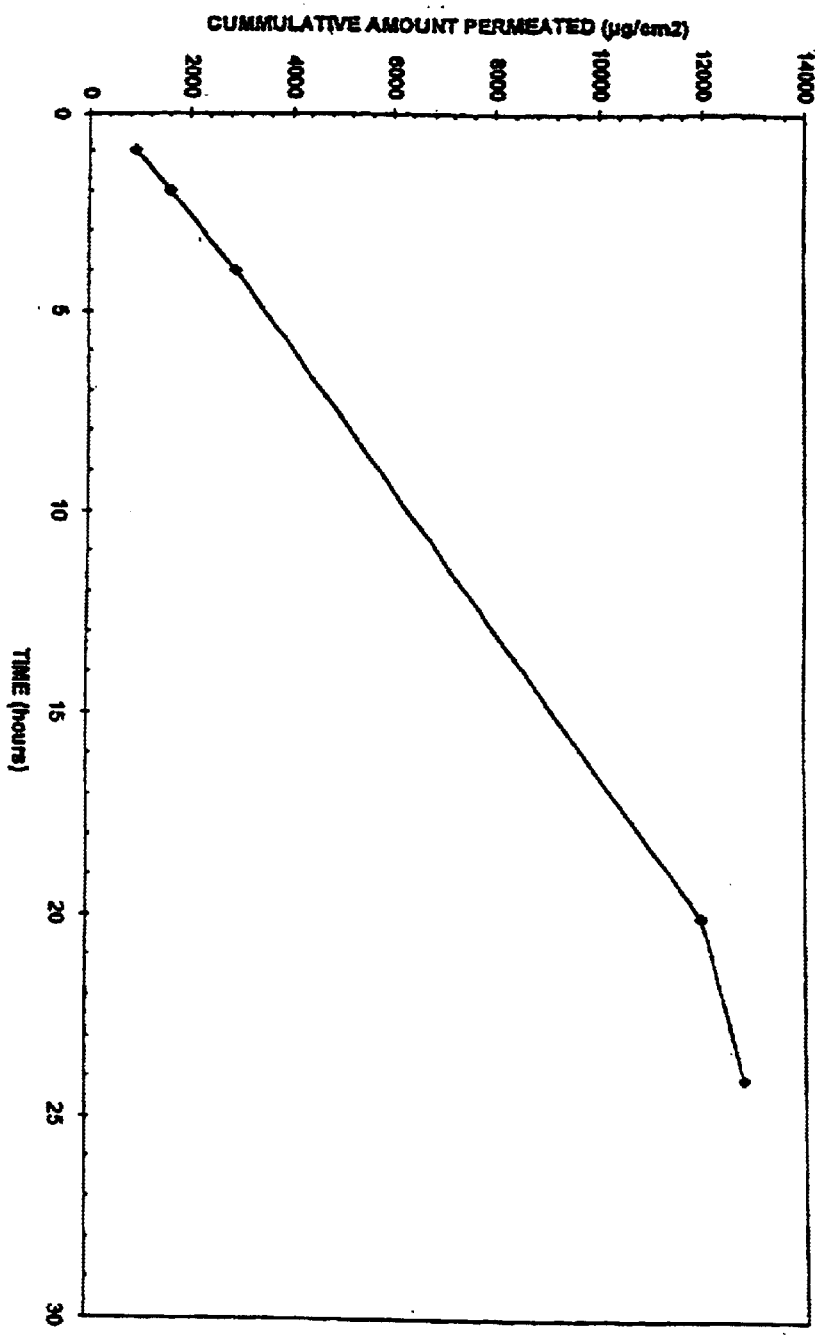
FIG. 8 is a graph showing the permeation of chlorpheniramine maleate from a buccal device in a diffusion test chamber.

The in vitro permeation profile is shown in FIG. 8. The flux can be calculated from this graph by determining its slope. For the pellet containing 10 mg of chlorpheniramine maleate, the average permeation rate through the mucosal tissue was 182 $\mu g/cm^2/hr$. For a pellet containing 5 mg of the drug, the average permeation rate through the mucosal tissue was 97.3 $\mu g/cm^2/hr$. This value is approximately half of that for the pellet containing 10 mg of chlorpheniramine maleate, indicating that these buccal devices (pellets) are not saturated with the drug. The flux of 182 $\mu g/cm^2/hr$ is adequate to produce systemic therapeutic levels since the oral daily dosage for chlorpheniramine maleate is 2 mg.

EXAMPLE 15

In this example, a dental device containing chlorhexidine diacetate was made. Silastic® (liquid silicone rubber: 7-6860) was obtained from Dow Corning. A paste was prepared with the following composition:

42% sodium alginate

16% chitosan

10% NOCC

32% Silastic® 7-6860

(All percentages are weight to weight.)

37.9 mg of chlorhexidine diacetate (Sigma Aldrich) was added to 410 mg of this paste with mixing. Chlorhexidine diacetate is a broad-spectrum anti-bacterial used for control of periodontal disease. Buccal-adhering devices were prepared as described in Example 10 using 60 mg portions of the mixture.

The device was 7 mm in diameter and 2–3 mm thick; it was durable and somewhat flexible. The device contained 9.15% NOCC and 5.08 mg of chlorhexidine diacetate and was adhesive to moist tissue.

EXAMPLE 16

In this example, an eye delivery device containing timolol maleate was made. Timolol maleate is a beta-blocker used to reduce pressure in the eye.

A paste was prepared with the following composition:

42% sodium alginate

16% chitosan

10% NOCC

32% Silastic® 7-6860 (Dow Corning)

(All percentages are weight to weight.) 19.7 mg of timolol maleate (Sigma Aldrich) was added to 243 mg of the paste (Sigma Aldrich) with mixing. Thin wafers were prepared using the press and techniques described in Example 10 but with 20 mg portions of the paste-drug mixture.

The device was 7 mm in diameter and less than 1 mm thick; it was durable and somewhat flexible. The device contained 9.25% NOCC and 1.50 mg of timolol maleate and was adhesive to moist tissue.

EXAMPLE 17

This example tested the permeation from the buccal device of Example 15.

The buccal-adhering devices, containing 5 mg of chlorhexidine diacetate, described in Example 15 were placed directly onto pieces of previously harvested rabbit large bowel that were mounted in Franz Diffusion Cells as described in Example 12. The permeation studies were conducted as described in Example 12 except that the analysis of the receptor solution was performed using a UV-Visible Spectrophotometer (Pharmacia Biotech Ultraspec 2000, set at a wavelength of 230 nm) and 3.0 ml aliquots were withdrawn at 0.5, 1, 2, 3, 4, 6, 18, and 24 hours.

Figure 9:
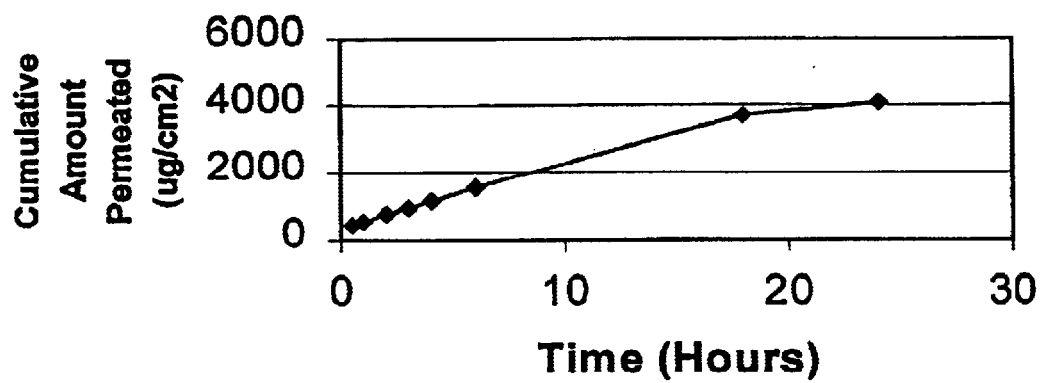
FIG. 9 is a graph showing the permeation of chlorhexidine diacetate from a buccal device in a diffusion test chamber.

The in vitro average (n=2) permeation profile is shown in FIG. 9. The flux can be calculated from this graph by determining its slope. For the device or pellet containing 5 mg of chlorhexidine diacetate, the average permeation rate through the mucosal tissue was 160.8 $\mu g/cm^2/hr$.

The flux of 160.8 $\mu g/cm^2/hr$ is adequate to produce a local therapeutic effect in local tissues. Hence, these devices are suitable for the delivery of drugs that are used to treat mouth sores and periodontal disease.

EXAMPLE 18

This example shows the permeation from the eye drug delivery device made in Example 16.

The wafers, containing 1.50 mg of timolol maleate, described in Example 16 were placed directly onto pieces of previously harvested rabbit large bowel that were mounted in Franz Diffusion Cells as described in Example 12. The permeation studies were conducted as described in Example 12 except that the analysis of the receptor solution was performed using a UV-Visible Spectrophotometer (Pharmacia Biotech Ultraspec 2000, set at a wavelength of 295 nm) and 3.ml aliquots were withdrawn at 0.5, 1, 2, 3, 4, 6, 18, and 24 hours.

Figure 10:
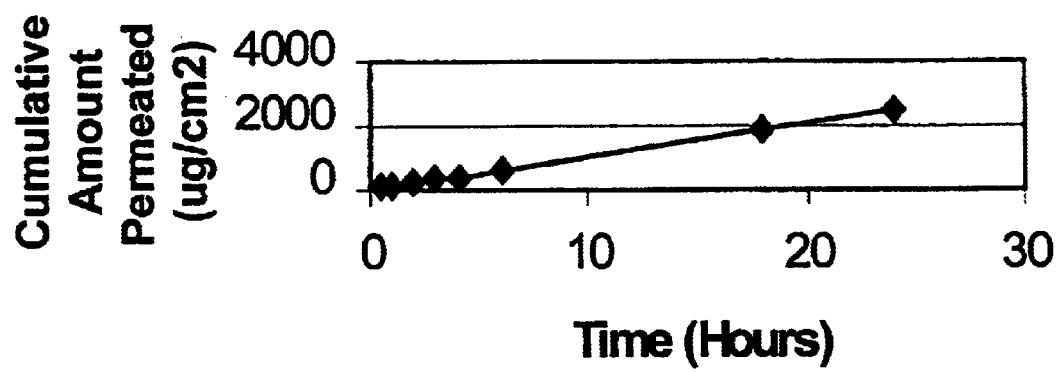
FIG. 10 is a graph showing the permeation of timolol maleate from an eye delivery device using a diffusion test chamber.

The in vitro average (n=2) permeation profile is shown in FIG. 10. The flux can be calculated from this graph by determining its slope. For the device or pellet containing 1.50 mg of timolol maleate, the average permeation rate through the mucosal tissue was 103.8 $\mu g/cm^2/hr$.

The flux of 103.8 $\mu g/cm^2/hr$ is adequate to produce a therapeutic effect to treat glaucoma when the wafer is inserted between the eye and eye lid. Hence, these devices are suitable for the delivery of drugs (such as beta blockers) to the eye.

EXAMPLE 19

In this example, an adherent formulation containing a fibrin sealant for prevention of surgical adhesions was prepared. A commercial 2-component fibrin sealant kit (Tisseel® Kit, Baxter Hyland Immuno) was used following the manufacturer's directions with one exception. The vial of protein concentrate (containing fibrinogen) was divided into portions that were reconstituted with either saline or NOCC solution (1.25% w/v). Thrombin was used at a level of 4 IU/ml for "slow solidification" according to the manufacturer's directions. The fibrin sealant with and without NOCC was applied to pieces of rabbit large bowel tissue. The tissues with sealant were cured for several minutes at 35–37 C° and inspected.

Within a few minutes the two different sealants had set and were no longer fluid. Both sealant mixtures adhered well to the underlying tissue. The sealant that incorporated NOCC was more viscous and remained in place better than the thinner, non-NOCC sealant that tended to flow away from the site of placement. The presence of NOCC slowed the setting time of the gel and yielded a more flexible material initially. The sealants covered the site of placement well and were no longer sticky on the exposed surface once they had cured.

Hence, the NOCC-containing sealant provides an improved adhesion barrier that remains at the site of application and forms a more flexible layer.

EXAMPLE 20

In this example, an adherent formulation containing a fibrin sealant for sealing or attaching tissues was prepared. A two component commercial fibrin sealant kit (Tisseel® Kit, Baxter Hyland immuno) was used to test for an adherent formulation with NOCC. The vial of protein concentrate (containing fibrinogen) was divided into portions that were reconstituted at 35 C° with either saline or NOCC solution (1.25% w/v). Freeze-dried thrombin was reconstituted with saline to yield a solution containing 13.9 IU/ml. Two ml of the thrombin solution was mixed with 2 ml of 10 mg/ml calcium chloride solution.

Fibrin sealant with and without NOCC was applied to rabbit large bowel tissue using the mixing dispenser supplied by the manufacturer. The tissues were approximately 1 inch square and the sealant was applied to half of the tissue. Immediately following the application of the sealant, the tissue was folded onto itself and pressed together lightly for 10–20 seconds. The tissues were kept warm (35–37 C.°) for 30 minutes and then evaluated.

In both cases, the tissues were firmly sealed together. There was more of the sealant containing NOCC within the folded tissue. The sealant that incorporated NOCC was more viscous and remained in place while the thinner non-NOCC sealant tended to flow away from the site of placement. The effort required to pull the folded tissue apart was somewhat greater for the NOCC containing sealant.

Hence, combining NOCC with other sealants forms improved products that effectively attach or seal tissues.

The foregoing examples are merely exemplary and those skilled in the art will be able to determine other modifications to the described procedures that fall within the scope of the invention. Accordingly, the invention is defined by the following claims and equivalents thereof.

What is claimed is:

1. A method of providing sustained release of a drug to moist tissue comprising applying to said moist tissue a drug delivery device which is adherent to said moist tissue and includes a level of N,O-carboxymethylchitosan as a component thereof to provide said adherence, said drug delivery device further containing a sufficient quantity of the drug to be delivered to provide sustained release of said drug and permeation into said moist tissue or into the surrounding cavity, wherein said moist tissue is mucosal tissue or a tissue in a serous cavity.

2. The method of claim 1, wherein said moist tissue comprises mucosal tissue.

3. The method of claim 2 wherein said mucosal tissue comprises tissue of the oral cavity.

4. The method of claim 3 wherein said oral cavity tissue comprises buccal tissue.

5. The method of claim 4 wherein said drug is selected from the group consisting of melatonin, chlorpheniramine, chlorhexidine, tetracycline and mixtures thereof.

6. The method of claim 3 wherein said device comprises a structural support material selected from the group consisting of rubber, plastic, resin natural and synthetic polymers, and mixtures thereof.

7. The method of claim 2 wherein said mucosal tissue comprises vaginal tissue.

8. The method of claim 7 wherein said drug is selected from a group consisting of progestins, estrogens, antifungal agents, antibacterial agents, anti-viral agents, proteins and peptides.

9. The method of claim 8 wherein said drug comprises levonorgestrel.

10. The method of claim 2 wherein said mucosal tissue comprises ocular tissue.

11. The method of claim 10 wherein said drug is selected from the group consisting of beta blockers and glaucoma treating drugs.

12. The method of claim 2 wherein said mucosal tissue comprises the gastrointestinal tract.

13. The method of claim 1 wherein said moist tissue is tissue in a serous cavity.

14. The method of claim 13 wherein said moist tissue is tissue within the pleural, pericardial or peritoneal cavities.

* * * * *